United States Patent
Higuchi et al.

(10) Patent No.: US 11,529,087 B2
(45) Date of Patent: Dec. 20, 2022

(54) ANAEROBIC THRESHOLD ESTIMATION METHOD AND DEVICE

(71) Applicant: Nippon Telegraph and Telephone Corporation, Tokyo (JP)

(72) Inventors: Yuichi Higuchi, Tokyo (JP); Hiroyoshi Togo, Tokyo (JP); Nobuaki Matsuura, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 210 days.

(21) Appl. No.: 17/046,046

(22) PCT Filed: Apr. 10, 2019

(86) PCT No.: PCT/JP2019/015577
§ 371 (c)(1),
(2) Date: Oct. 8, 2020

(87) PCT Pub. No.: WO2019/198742
PCT Pub. Date: Oct. 17, 2019

(65) Prior Publication Data
US 2021/0030296 A1 Feb. 4, 2021

(30) Foreign Application Priority Data
Apr. 12, 2018 (JP) .............................. JP2018-076549

(51) Int. Cl.
*A61B 5/352* (2021.01)
*A61B 5/0245* (2006.01)
*A61B 5/11* (2006.01)

(52) U.S. Cl.
CPC ............ *A61B 5/352* (2021.01); *A61B 5/0245* (2013.01); *A61B 5/1118* (2013.01)

(58) Field of Classification Search
None
See application file for complete search history.

(56) References Cited

U.S. PATENT DOCUMENTS

| 4,622,980 A | 11/1986 | Kunig |
| 8,755,872 B1 | 6/2014 | Marinow |

(Continued)

FOREIGN PATENT DOCUMENTS

| EP | 2732758 A1 | 5/2014 |
| JP | 2004000646 A | 1/2004 |

(Continued)

OTHER PUBLICATIONS

Cardia Nursing Educational Society, "Basic electrocardiogram Waveform, Normal value of ECG Waveform," http://www.cardiac.jp/view.php?lang=ja&target=normal_ecg_pattern.XML, 2004, searched on Mar. 7, 2018 and as described in the specification, 5 pages.

(Continued)

*Primary Examiner* — Ankit D Tejani
(74) *Attorney, Agent, or Firm* — Slater Matsil, LLP

(57) ABSTRACT

A method includes a first acquisition step of acquiring exercise intensity of exercise done by a target person, a second acquisition step of acquiring an electrocardiographic waveform of the target person who does the exercise, a third acquisition step of acquiring a predetermined feature amount from the acquired electrocardiographic waveform, and an estimation step of estimating an AT of the target person based on a relationship between the predetermined feature amount and the acquired exercise intensity. The estimation step includes a step of estimating the AT of the target person based on exercise intensity corresponding to an inflection point in a change of the predetermined feature amount with respect to the acquired exercise intensity.

12 Claims, 3 Drawing Sheets

(56) References Cited

U.S. PATENT DOCUMENTS

2017/0000415 A1* 1/2017 Lapetina .............. A61B 5/0205
2019/0038219 A1 2/2019 Kim et al.

FOREIGN PATENT DOCUMENTS

| JP | 2004275281 A | 10/2004 |
| --- | --- | --- |
| JP | 2015173768 A | 10/2015 |
| JP | 2016214872 A | 12/2016 |
| JP | 2017029258 A | 2/2017 |

OTHER PUBLICATIONS

Wasserman "Principle of measurement method of exercise physiology and data interpretation (endurance)", Anaerobic Threshold: AT, http://sugp.wakasato.jp/Material/Medicine/cai/text/subject02/no8/html/section9.html, 1985, searched on Mar. 1, 2018 and as described in the specification, 5 pages.

Wikipedia, "Electro-Cardiogram," https://ja.wikipedia.org/wiki/%E5%BF%83%E9%9B%BB%E5%9B%B3, searched on Mar. 7, 2018 and as described in the specification, 35 pages.

Fudin, et al., "Relationship between the Parameters of Muscular and Cardiovascular Systems in Graded Exercise Testing in Subjects Doing Regular Exercises and Sports," Human Physiology, 2015, vol. 41, No. 4, pp. 412-419.

* cited by examiner

ANAEROBIC THRESHOLD ESTIMATION METHOD AND DEVICE

CROSS-REFERENCE TO RELATED APPLICATIONS

This application is a national phase entry of PCT Application No. PCT/JP2019/015577, filed on Apr. 10, 2019, which claims priority to Japanese Application No. 2018-076549, filed on Apr. 12, 2018, which applications are hereby incorporated herein by reference.

TECHNICAL FIELD

The present invention relates to an anaerobic threshold estimation method and device and, more particularly, to a technique of estimating an anaerobic threshold using an electrocardiographic waveform.

BACKGROUND

In sports and daily life, a target person can appropriately train by managing the exercise state of the target person. As a value for managing the exercise state of the target person, an anaerobic threshold (to be referred to as an "AT" hereinafter) is known.

The AT indicates exercise intensity as a change point at which aerobic exercise is switched to anaerobic exercise (see, for example, non-patent literature 1). It is said that if a target person trains at exercise intensity higher than the AT, the ability of anaerobic exercise is improved, and if the target person trains at exercise intensity lower than the AT, the ability of aerobic exercise is improved.

Conventionally, the AT has been measured by various methods, and is called a lactate threshold (to be referred to as an "LT" hereinafter) when a lactic acid value is used as a reference. When the concentration of carbon dioxide gas in expiration is used as a reference, the AT is called a ventilatory threshold (to be referred to as a "VT" hereinafter).

RELATED ART LITERATURE

Non-Patent Literature

Non-Patent Literature 1:
http://sugp.wakasato.jp/Material/Medicine/cai/text/subject02/n08/html/section9.html (searched on Mar. 1, 2018)
Non-Patent Literature 2:
https://ja.wikipedia.org/wiki/%E5%BF%83%E9%9B%BB%E5%9B%B3 (searched on Mar. 7, 2018)
Non-Patent Literature 3:
http://www.cardiac.jp/view.php?lang=ja&target=normal_ecg_pattern.xml (searched on Mar. 7, 2018).

SUMMARY

Problem to be Solved by Embodiments of the Invention

However, in conventional measurement of the LT, it is necessary to collect blood although a collection amount is small, and it is thus difficult to measure the LT all the time. In addition, in conventional measurement of the LT, a large-scale device and a mask for collecting expired gas are necessary, and it is thus difficult to measure the VT easily. Consequently, the conventional technique cannot measure the AT easily.

Embodiments of the present invention have been made in consideration of the above problems, and has as its object to provide an anaerobic threshold estimation method and device capable of estimating the AT of a target person more easily.

Means of Solution to the Problem

In order to solve the above problems, according to embodiments of the present invention, there is provided an anaerobic threshold estimation method comprising a first acquisition step of acquiring exercise intensity of exercise done by a target person, a second acquisition step of acquiring an electrocardiographic waveform of the target person who does the exercise, a third acquisition step of acquiring a predetermined feature amount from the acquired electrocardiographic waveform, and an estimation step of estimating an anaerobic threshold of the target person based on a relationship between the predetermined feature amount and the acquired exercise intensity, wherein the estimation step includes a step of estimating the anaerobic threshold of the target person based on exercise intensity corresponding to an inflection point in a change of the predetermined feature amount with respect to the acquired exercise intensity.

According to embodiments of the present invention, there is also provided an anaerobic threshold estimation device comprising an exercise intensity acquisition unit configured to acquire exercise intensity of exercise done by a target person, a feature amount acquisition unit configured to acquire an electrocardiographic waveform of the target person who does the exercise, and acquire a predetermined feature amount from the electrocardiographic waveform, and an estimation unit configured to estimate an anaerobic threshold of the target person based on a relationship between the predetermined feature amount and the acquired exercise intensity, wherein the estimation unit estimates the anaerobic threshold of the target person based on exercise intensity corresponding to an inflection point in a change of the predetermined feature amount with respect to the acquired exercise intensity.

Effect of Embodiments of the Invention

According to embodiments of the present invention, from the relationship between a predetermined feature amount in the electrocardiographic waveform of a target person who does exercise and the exercise intensity of the exercise done by the target person, an inflection point in a change of the feature amount with respect to the exercise intensity is extracted, and then an AT is calculated based on information of the inflection point. Thus, it is possible to estimate the AT of the target person more easily.

DETAILED DESCRIPTION OF ILLUSTRATIVE EMBODIMENTS

An embodiment of the present invention will be described in detail below with reference to FIGS. 1 to 6.

Principles of Embodiments of Invention

Figure 1:
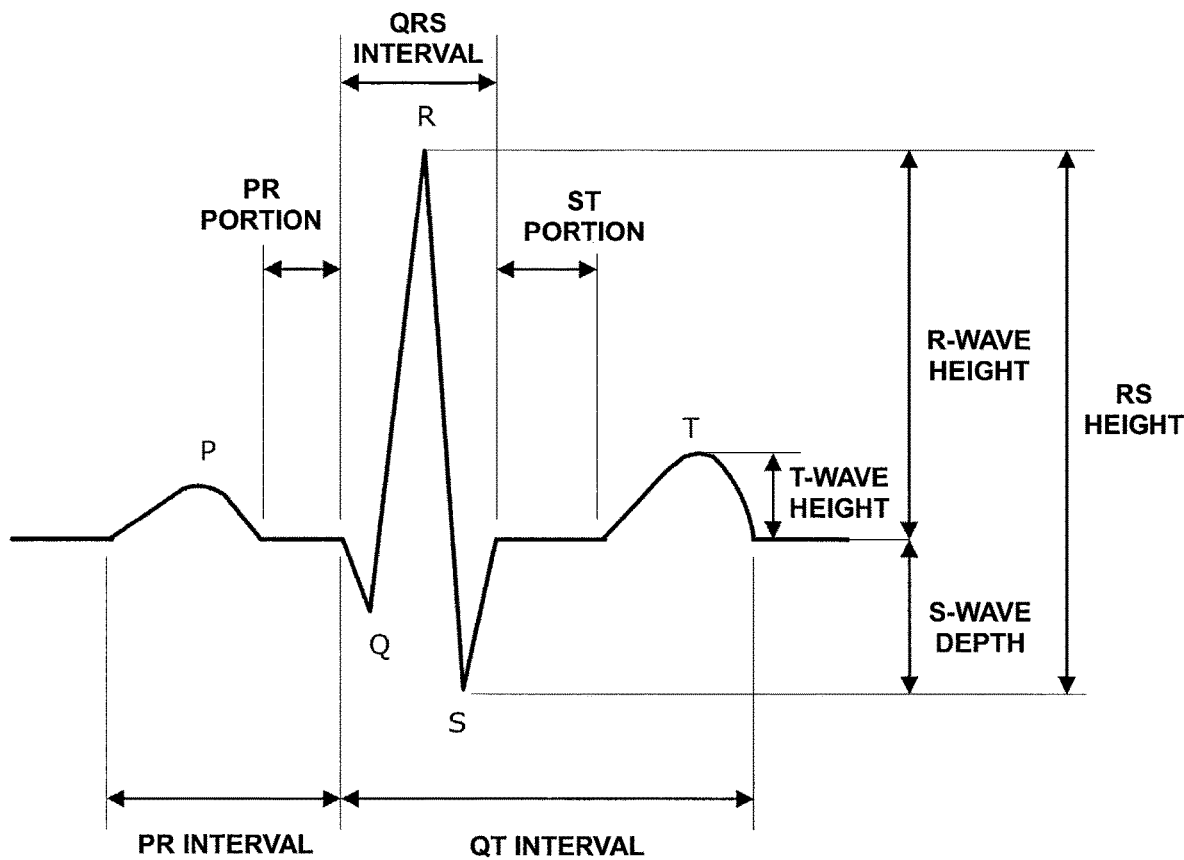
FIG. 1 is a view for explaining the principles of embodiments of the present invention.

FIG. 1 is a view showing an electrocardiographic waveform (see non-patent literatures 2 and 3). An AT estimation method according to the embodiment of the present invention extracts a predetermined feature amount serving as an index from the electrocardiographic waveform of a target person, and estimates an AT for managing the exercise state of the target person based on the feature amount.

In the AT estimation method according to this embodiment, among characteristic waveforms and waveform intervals included in the electrocardiographic waveform shown in FIG. 1, the height of a T wave is used as a feature amount of the electrocardiographic waveform (electrocardiogram) (see non-patent literatures 1 and 2).

Figure 2:
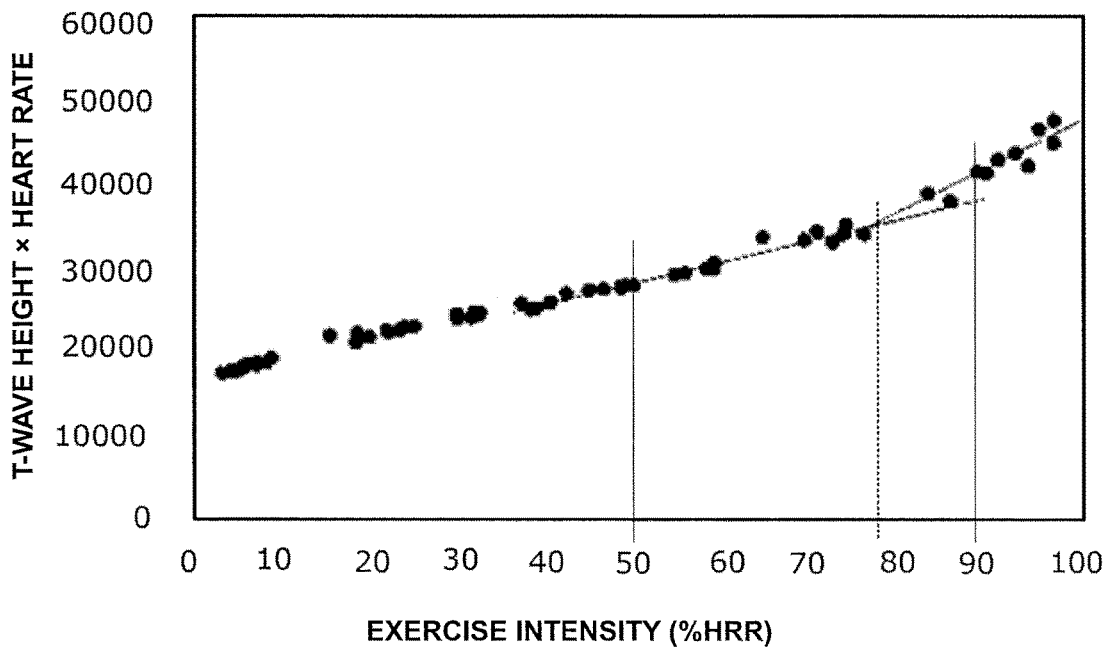
FIG. 2 is a graph for explaining the principles of an AT estimation device according to an embodiment of the present invention.

FIG. 2 is a graph showing the relationship between exercise intensity and the product (T-wave height×heart rate) of a heart rate and a T-wave height acquired by an incremental load test. In this embodiment, a heart rate reserve (HRR), a value calculated from a heart rate by the Karvonen method, is used as the exercise intensity. Note that the exercise intensity is a scale representing the vigorousness of exercise with reference to the physical ability of the target person who does the exercise.

As indicated by a dotted line in FIG. 2, it is apparent that there is an inflection point in the graph around a portion where the exercise intensity is 80%. An experiment indicates that the exercise intensity at the inflection point of the value of "T-wave height×heart rate" is set as an AT.

Figure 3:
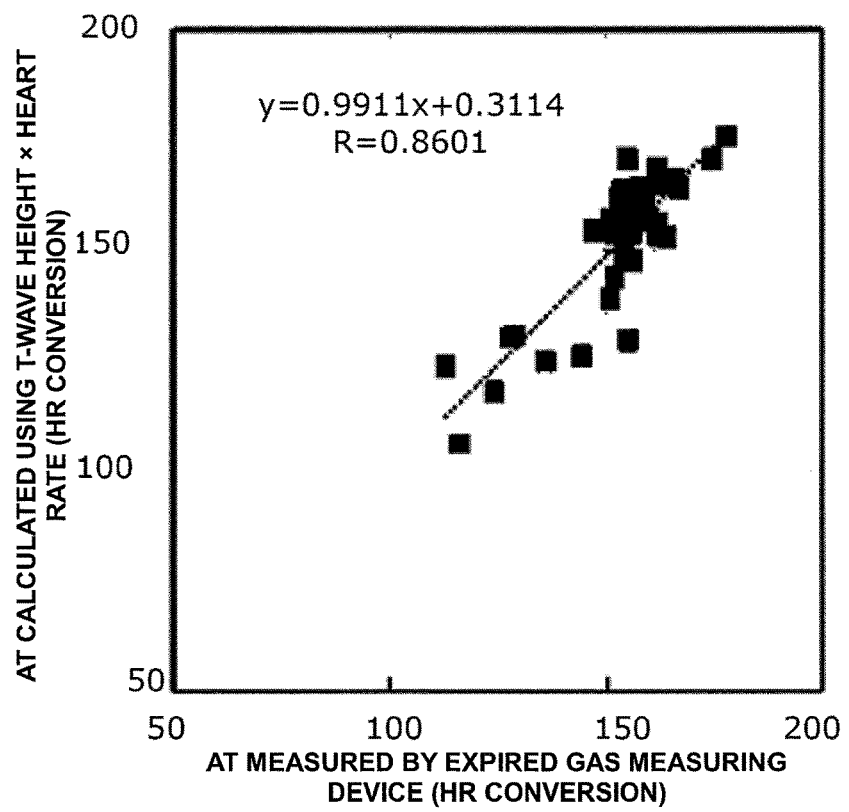
FIG. 3 is a graph for explaining the principles of the AT estimation device according to the embodiment of the present invention.

FIG. 3 is a graph obtained by converting the AT calculated using "T-wave height×heart rate" and an AT measured by an expired gas measuring device into heart rates (bpm) and comparing them. In FIG. 3, the ordinate represents the AT estimated by the AT estimation method according to this embodiment and the abscissa represents the AT measured by the expired gas measuring device.

As shown in FIG. 3, since a correlation function is R=0.86 and p<0.05 is satisfied, the AT calculated using "T-wave height×heart rate" and the AT measured by the expired gas measuring device have a significant positive correlation. It is thus understood that the AT estimation method according to this embodiment can estimate the AT by finding the inflection point of the value of "T-wave height×heart rate" in the relationship between "T-wave height×heart rate" and the exercise intensity.

Embodiment

An AT estimation device 1 for executing the AT estimation method according to embodiments of the present invention will be described in detail below.

Figure 4:
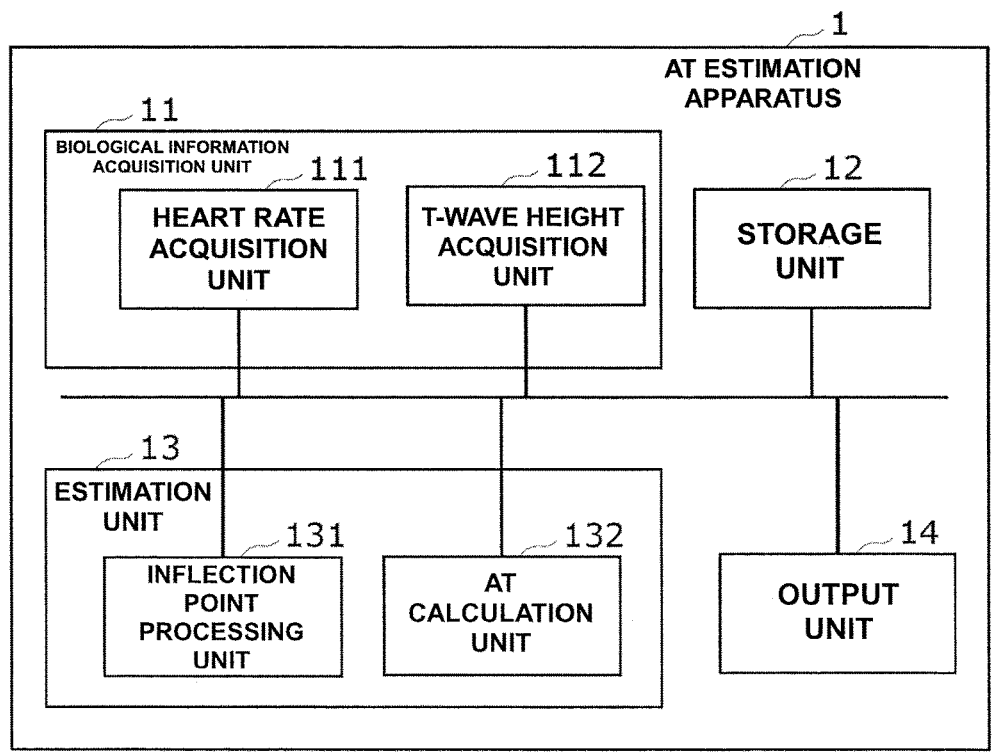
FIG. 4 is a block diagram showing the functional arrangement of the AT estimation device according to the embodiment of the present invention.

FIG. 4 is a block diagram showing the functional arrangement of the AT estimation device 1 according to the first embodiment. The AT estimation device 1 includes a biological information acquisition unit 11, a storage unit 12, an estimation unit 13, and an output unit 14.

The AT estimation device 1 obtains the relationship between "T-wave height×heart rate" and exercise intensity when a target person does exercise like an incremental load test that gradually increases exercise intensity. The AT estimation device 1 extracts the inflection point of the value of "T-wave height×heart rate", and calculates exercise intensity at the inflection point as an AT. As described above, in the relationship between "T-wave height×heart rate" and the exercise intensity, the inflection point exists around a portion where the value of the exercise intensity is 80%, more specifically, within the range of 50% to 90%, as shown in FIG. 2.

The biological information acquisition unit 11 includes a heart rate acquisition unit (exercise intensity acquisition unit) 111 and a T-wave height acquisition unit (feature amount acquisition unit) 112.

The biological information acquisition unit 11 acquires information concerning the heart beats and electrocardiogram of the target person from an external biological sensor (not shown) having the functions of the heart rate meter and electrocardiograph and attached to the target person. At this time, the biological information acquisition unit 11 acquires, from the above-described experiment result, information concerning the heartbeats and electrocardiogram for a period from when the target person starts exercise that gradually increases the exercise intensity until the exercise intensity becomes about 90%.

The heart rate acquisition unit 111 acquires, from the biological sensor attached to the target person, a heart rate for a period during which the target person does exercise like an incremental load test that gradually increases the exercise intensity. Data of the acquired heart rate is stored in the storage unit 12.

The T-wave height acquisition unit 112 acquires T-wave height data in the electrocardiographic waveform from the electrocardiographic waveform of the target person measured by the biological sensor attached to the target person. The T-wave height acquisition unit 112 obtains a value (T-wave height×heart rate) by multiplying the acquired value of the T-wave height of the target person by the heart rate acquired by the heart rate acquisition unit 111. The data of "T-wave height×heart rate" obtained by the T-wave height acquisition unit 112 is stored in the storage unit 12.

The T-wave height acquisition unit 112 can acquire, from the electrocardiographic waveform of the target person, an RS height indicating the height from the peak value of an R wave to that of an S wave, as shown in FIG. 1, and normalize the T-wave height by the RS height. The T-wave height acquisition unit 112 can obtain "T-wave height×heart rate" based on the T-wave height corrected by normalization using the RS height. Alternatively, the T-wave height acquisition unit 112 may normalize the T-wave height by an R-wave height or an S-wave depth, and use it.

The storage unit 12 stores the data of "T-wave height× heart rate" and the heart rate of the target person acquired by the biological information acquisition unit 11.

The estimation unit 13 includes an inflection point processing unit 131 and an AT calculation unit 132.

The estimation unit 13 estimates the AT of the target person based on the data of "T-wave height×heart rate" and the heart rate of the target person acquired by the biological information acquisition unit 11.

The inflection point processing unit 131 reads out, from the storage unit 12, the data of the heart rate of the target person acquired by the heart rate acquisition unit 111 and the data of "T-wave height×heart rate" obtained by the T-wave height acquisition unit 112, and obtains the relationship between "T-wave height×heart rate" and the exercise intensity. At this time, the relationship shown in FIG. 2 is obtained.

Furthermore, the inflection point processing unit 131 extracts, from the relationship between "T-wave height× heart rate" and the exercise intensity of the target person, an inflection point in a change of "T-wave height×heart rate" with respect to the heart rate acquired by the heart rate acquisition unit 111. The inflection point falls within the range of 50% to 90% of exercise intensity. The inflection point processing unit 131 obtains the exercise intensity of the target person corresponding to the inflection point of the value of "T-wave height×heart rate", and stores it in the storage unit 12.

The AT calculation unit 132 calculates the AT of the target person based on the exercise intensity of the target person at the inflection point extracted by the inflection point processing unit 131.

More specifically, the AT calculation unit 132 calculates, as the AT, the exercise intensity of the target person at the inflection point extracted by the inflection point processing unit 131.

The AT calculation unit 132 stores the calculated AT value of the target person in the storage unit 12.

The output unit 14 outputs information such as the AT of the target person estimated by the estimation unit 13. More specifically, the output unit 14 displays the AT value calculated by the AT calculation unit 132 on a display screen or the like.

Hardware Arrangement of AT Estimation Device

The hardware arrangement of the AT estimation device 1 having the above-described functional arrangement will be described next with reference to a block diagram shown in FIG. 5.

Figure 5:
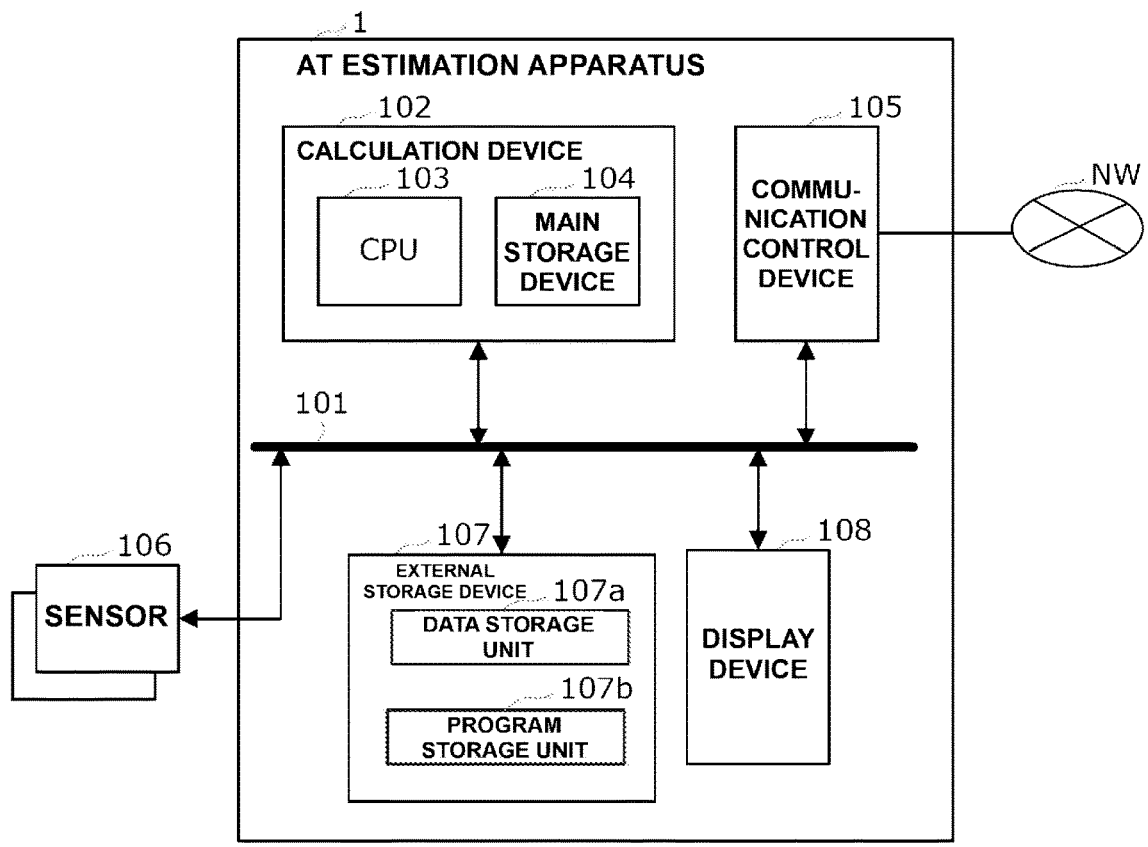
FIG. 5 is a block diagram showing the hardware arrangement of the AT estimation device according to the embodiment of the present invention.

As shown in FIG. 5, the AT estimation device 1 can be implemented by a computer including a calculation device 102 with a CPU 103 and a main storage device 104, a communication control device 105, a sensor 106, an external storage device 107, and a display device 108, all of which are connected via a bus 101, and a program for controlling these hardware resources.

The CPU 103 and the main storage device 104 form the calculation device 102. A program used by the CPU 103 to perform various control and calculation operations is stored in advance in the main storage device 104. The calculation device 102 implements the respective functions of the AT estimation device 1 including the estimation unit 13 shown in FIG. 4.

The communication control device 105 is a control device for connecting the AT estimation device 1 and various external electronic devices by a communication network NW. The communication control device 105 may receive, via the communication network NW, the data of the heart rate and electrocardiograph waveform from the sensor 106 (to be described later) attached to the target person.

The sensor 106 is implemented by, for example, a biological sensor such as a heart rate meter and an electrocardiograph. The sensor 106 is attached to, for example, the chest or wrist of the target person for a period during which the target person does exercise, and measures the heart rate and the electrocardiographic waveform of the target person. For example, the sensor 106 attached to the chest measures the electrocardiographic waveform by an electrode (not shown), and detects heartbeats from a change of the electrocardiographic waveform, thereby measuring, as a heart rate, a heartbeat count per minute from an interval between the heartbeats.

The external storage device 107 is formed by a readable/writable storage medium and a driving device for reading/writing various kinds of information such as programs and data from/in the storage medium. For the external storage device 107, a hard disk or a semiconductor memory such as a flash memory can be used as a storage medium. The external storage device 107 can include a data storage unit 107a, a program storage unit 107b, and another storage device (not shown), for example, a storage device for backing up the programs and data stored in the external storage device 107.

The data storage unit 107a stores information concerning the electrocardiographic waveform and the heart rate of the target person measured by the sensor 106. The data storage unit 107a corresponds to the storage unit 12 shown in FIG. 4.

The program storage unit 107b stores various programs for executing processing necessary to estimate the AT, such as processing of acquiring the heart rate and T-wave height, inflection point processing, and AT calculation processing, according to this embodiment.

The display device 108 forms the display screen of the AT estimation device 1, and functions as the output unit 14. The display device 108 is implemented by a liquid crystal display or the like.

Operation of AT Estimation Device

Figure 6:
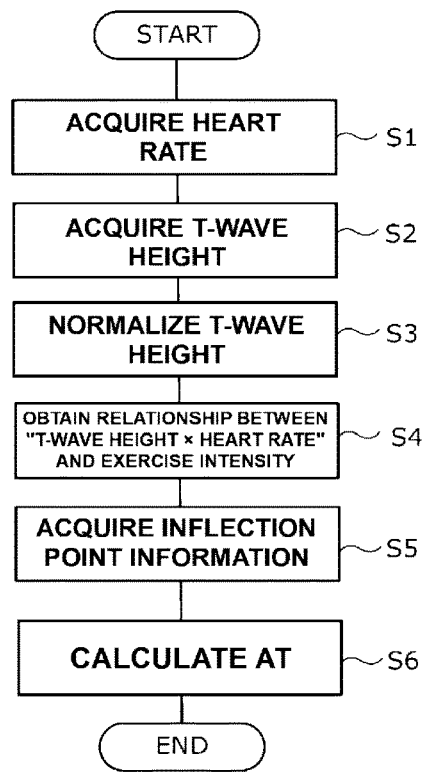
FIG. 6 is a flowchart for explaining an AT estimation method according to the embodiment of the present invention.

The operation of the AT estimation device 1 for executing the above-described AT estimation method according to embodiments of the present invention will be described next with reference to a flowchart shown in FIG. 6. First, a biological sensor (not shown) having the functions of the heart rate meter and electrocardiograph is attached to the chest or wrist of a target person, and the target person starts exercise set to gradually increase exercise intensity like an incremental load test. The biological sensor measures the heart rate and electrocardiographic waveform of the target person for a period from when the target person starts exercise until the exercise intensity of the target person exceeds, for example, 90%.

The heart rate acquisition unit 111 acquires heart rate data for a period during which the target person does the exercise (step S1). Next, the T-wave height acquisition unit 112 acquires electrocardiographic waveform data for a period during which the target person does the exercise, and acquires T-wave height data from the electrocardiographic waveform data (step S2).

Next, the T-wave height acquisition unit 112 acquires, from the electrocardiographic waveform data, an RS height from the peak value of an R wave to that of an S wave, and obtains data of "T-wave height×heart rate" based on the T-wave height normalized by the RS height (step S3). Note that the T-wave height acquisition unit 112 may adopt an arrangement of acquiring the measured value of the T-wave height obtained by the external biological sensor, the value of "T-wave height×heart rate", or the value of "T-wave height×heart rate" normalized by the RS height.

Next, the inflection point processing unit 131 obtains the relationship between the obtained value of "T-wave height× heart rate" and exercise intensity converted by the heart rate (step S4). In the relationship between "T-wave height×heart rate" and the exercise intensity of the target person, which has been obtained by the inflection point processing unit 131, the inflection point of the value of "T-wave height× heart rate" is extracted, and exercise intensity corresponding to the value of "T-wave height×heart rate" at the inflection point is obtained (step S5). As described above, based on the fact that the inflection point is extracted within the range of 50% to 90% of exercise intensity, it is possible to use only the range of 50% to 90% with respect to the value of exercise intensity.

Next, the AT calculation unit 132 calculates the AT based on the value of the exercise intensity at the inflection point of the value of "T-wave height×heart rate" obtained in step S4 (step S6). That is, the AT calculation unit 132 obtains, as the AT, the value of the exercise intensity at the inflection point. Note that the output unit 14 outputs the calculated AT of the target person. Furthermore, the output unit 14 may convert the exercise intensity obtained as the AT into another index, for example, a heart rate (bpm) or power (watt), and output it.

As described above, according to this embodiment, the T-wave height in the electrocardiographic waveform of the target person is used as a feature amount. In addition, based on the relationship between "T-wave height×heart rate" and exercise intensity, the AT of the target person is estimated from the value of the exercise intensity at the inflection point of the value of "T-wave height×heart rate" within the range of about 50% to 90% of the exercise intensity. Therefore, it is possible to estimate the AT of the target person more easily without requiring blood collection or any large-scale device.

Furthermore, by calculating the AT using data within the range of 50% to 90% of the value of the exercise intensity in which the inflection point is more highly probably extracted, as described above, it is possible to reduce the calculation amount when calculating the AT.

Since the T-wave height is corrected by normalization using the RS height, R-wave height, or S-wave depth, it is possible to calculate the AT based on the more correct T-wave height even if noise is included due to, for example, wetting of the electrode of the electrocardiograph with sweat or the like.

Note that the above-described embodiment has explained the case in which the exercise intensity calculated from the heart rate (HR) is used. However, the exercise intensity is not limited to the heart rate, and may change its type depending on the acquired data and the type of exercise, such as power, speed, and the number of rotations.

The above-described embodiment has explained the case in which the target person does exercise like an incremental load test and data concerning a heart rate and an electrocardiographic waveform for an exercise period is acquired. However, the exercise done by the target person is not limited to the incremental load test, and may be, for example, random exercise. Even if the target person does random exercise, "T-wave height×heart rate" is obtained from the electrocardiographic waveform of the target person, and the relationship between "T-wave height×heart rate" and exercise intensity is obtained in the same manner.

In the above-described embodiment, the relationship with exercise intensity is obtained using the data of "T-wave height×heart rate" of the target person. However, even using only the T wave, an inflection point can be similarly extracted from the relationship with exercise intensity, and the value of corresponding exercise intensity can be calculated as the AT.

Similarly, the R-wave height that changes depending on exercise of the target person like the T-wave height may be used as a feature amount.

The embodiment in the anaerobic threshold estimation method and anaerobic threshold estimation device according to the present invention has been described above. However, the present invention is not limited to the above-described embodiment, and various modifications conceivable by those skilled in the art can be made within the scope of the invention described in the claims.

EXPLANATION OF THE REFERENCE NUMERALS AND SIGNS

1 . . . AT estimation device, 11 . . . biological information acquisition unit, 12 . . . storage unit, 13 . . . estimation unit, 14 . . . output unit, 111 . . . heart rate acquisition unit, 112 . . . T-wave height acquisition unit, 131 . . . inflection point processing unit, 132 . . . AT calculation unit, 101 . . . bus, 102 . . . calculation device, 103 . . . CPU, 104 . . . main storage device, 105 . . . communication control device, 106 . . . sensor, 107 . . . external storage device, 107a . . . data storage unit, 107b . . . program storage unit, 108 . . . display device, NW . . . communication network.

The invention claimed is:

1. An anaerobic threshold estimation method comprising:
acquiring exercise intensity of exercise done by a target person;
acquiring an electrocardiographic waveform of the target person;
acquiring a predetermined feature amount from the electrocardiographic waveform; and
estimating an anaerobic threshold of the target person based on a relationship between the predetermined feature amount and the exercise intensity, wherein estimating the anaerobic threshold comprises estimating the anaerobic threshold of the target person based on exercise intensity corresponding to an inflection point in a change of the predetermined feature amount with respect to the exercise intensity, wherein the predetermined feature amount is a height of a T wave included in the electrocardiographic waveform multiplied by a heart rate.

2. The anaerobic threshold estimation method according to claim 1, wherein the predetermined feature amount is a height of an R wave included in the electrocardiographic waveform.

3. The anaerobic threshold estimation method according to claim 1, wherein the exercise intensity acquired is a value of exercise intensity calculated from a heart rate.

4. The anaerobic threshold estimation method according to claim 1, wherein estimating the anaerobic threshold of the target person comprises estimating the anaerobic threshold of the target person using the inflection point at which the value of the exercise intensity falls within a range of 50% to 90% in the relationship between the predetermined feature amount and the exercise intensity.

5. The anaerobic threshold estimation method according to claim 1, wherein acquiring the predetermined feature amount comprises:
acquiring an RS height from a peak value of an R wave to a peak value of an S wave, wherein the R wave and the S wave are included in the electrocardiographic waveform; and
normalizing the height of the T wave using the RS height, a height of the R wave, or a depth of the S wave.

6. An anaerobic threshold estimation method comprising:
acquiring exercise intensity of exercise done by a target person;
acquiring an electrocardiographic waveform of the target person;
acquiring a predetermined feature amount from the electrocardiographic waveform; and estimating an anaerobic threshold of the target person based on a relationship between the predetermined feature amount and the exercise intensity, wherein estimating the anaerobic threshold comprises estimating the anaerobic threshold of the target person based on exercise intensity corresponding to an inflection point in a change of the predetermined feature amount with respect to the exercise intensity, wherein the predetermined feature amount is a height of a T wave included in the electrocardiographic waveform, and wherein acquiring the predetermined feature amount comprises:

acquiring an RS height from a peak value of an R wave to a peak value of an S wave, wherein the R wave and the S wave are included in the electrocardiographic waveform; and normalizing the height of the T wave using the RS height, a height of the R wave, or a depth of the S wave.

7. An anaerobic threshold estimation device comprising:
one or more processors; and
a non-transitory computer-readable storage medium storing a program to be executed by the one or more processors, the program including instructions for:
    acquiring exercise intensity of exercise done by a target person;
    acquiring an electrocardiographic waveform of the target person;
    acquiring a predetermined feature amount from the electrocardiographic waveform; and
    estimating an anaerobic threshold of the target person based on a relationship between the predetermined feature amount and the exercise intensity, the anaerobic threshold of the target person is estimated based on exercise intensity corresponding to an inflection point in a change of the predetermined feature amount with respect to the exercise intensity, wherein the predetermined feature amount is a height of the T wave included in an electrocardiographic waveform multiplied by a heart rate.

8. The anaerobic threshold estimation device according to claim 7, wherein the instructions include further instructions for:
    acquiring an RS height from a peak value of an R wave to a peak value of an S wave, wherein the R wave and the S wave are included in the electrocardiographic waveform; and
    normalizing the height of the T wave using the RS height, a height of the R wave, or a depth of the S wave.

9. The anaerobic threshold estimation device according to claim 7, wherein the predetermined feature amount is a height of an R wave included in the electrocardiographic waveform.

10. The anaerobic threshold estimation device according to claim 7, wherein the exercise intensity is a value of exercise intensity calculated from a heart rate.

11. The anaerobic threshold estimation device according to claim 7, wherein the anaerobic threshold of the target person is estimated using the inflection point at which the value of the exercise intensity falls within a range of 50% to 90% in the relationship between the predetermined feature amount and the exercise intensity.

12. An anaerobic threshold estimation device comprising:
one or more processors; and
a non-transitory computer-readable storage medium storing a program to be executed by the one or more processors, the program including instructions for:
    acquiring exercise intensity of exercise done by a target person;
    acquiring an electrocardiographic waveform of the target person;
    acquiring a predetermined feature amount from the electrocardiographic waveform;
    estimating an anaerobic threshold of the target person based on a relationship between the predetermined feature amount and the exercise intensity, the anaerobic threshold of the target person is estimated based on exercise intensity corresponding to an inflection point in a change of the predetermined feature amount with respect to the exercise intensity, wherein the predetermined feature amount is a height of a T wave included in the electrocardiographic waveform;
    acquiring an RS height from a peak value of an R wave to a peak value of an S wave, wherein the R wave and the S wave are included in the electrocardiographic waveform; and
    normalizing the height of the T wave using the RS height, a height of the R wave, or a depth of the S wave.

\* \* \* \* \*